United States Patent [19]

Christy

[11] 4,017,543

[45] Apr. 12, 1977

[54] α,α-DIALKYL-4-PHENETHYL-BENZYLAMINES AND THE SALTS THEREOF

[75] Inventor: Marcia Elizabeth Christy, Perkasie, Pa.

[73] Assignee: Merck & Co., Inc., Rahway, N.J.

[22] Filed: Oct. 23, 1975

[21] Appl. No.: 625,279

Related U.S. Application Data

[63] Continuation of Ser. No. 426,170, Dec. 19, 1973, abandoned, which is a continuation-in-part of Ser. No. 205,708, Dec. 7, 1971, abandoned, which is a continuation-in-part of Ser. No. 106,389, Jan. 15, 1971, abandoned.

[52] U.S. Cl. .................. 260/570.8 R; 260/465 R; 260/471 R; 260/471 C; 260/556 AR; 260/501.1; 260/501.18; 260/558 R; 260/558 D; 260/562 P; 260/665 G; 260/551 R; 424/316; 424/330
[51] Int. Cl.$^2$ ........................................ C07C 87/28
[58] Field of Search ................ 260/570.9, 570.8 R, 260/501.1, 501.21

[56] References Cited

UNITED STATES PATENTS

| | | | |
|---|---|---|---|
| 3,309,404 | 3/1967 | Engelhardt | 260/556 |
| 3,719,712 | 3/1973 | Remy | 260/570.9 |
| 3,780,106 | 5/1974 | Trent et al. | 260/570.8 X |
| 3,819,723 | 6/1974 | Dvolaitzky et al. | 260/570.8 X |

OTHER PUBLICATIONS

Klein et al., "Journal Organic Chemistry", vol. 32, pp. 1155–1160 (1967).

*Primary Examiner*—Robert V. Hines
*Attorney, Agent, or Firm*—Daniel T. Szura; Thomas E. Arthur; Harry E. Westlake, Jr.

[57] ABSTRACT

This application discloses methods of preparing α,α-diloweralkyl substituted benzylamines by the catalytic hydrogenation of the corresponding α,α-dialkyl-4-(phenyl-ethynyl)-benzylamine. The produced α,α-diloweralkylamines are converted to the corresponding N-alkyl and N,N-dialkyl derivatives thereof. The amines and their alkylated derivatives are useful as antiarrhythmics.

9 Claims, No Drawings

α,α-DIALKYL-4-PHENETHYL-BENZYLAMINES AND THE SALTS THEREOF

This is a continuation of Ser. No. 426,170, filed Dec. 19, 1973, and now abandoned which application in turn is a continuation-in-part of application Ser. No. 205,708, filed Dec. 7, 1971 now abandoned, which application in turn is a continuation-in-part of application Ser. No. 106,889, filed Jan. 15, 1971, now abandoned.

This invention relates to derivatives of aralkylamine compounds. More specifically, it relates to substituted derivatives of phenethylbenzylamines, phenethylphenethylamines, and the corresponding N-substituted derivatives such as the N-alkyl and the N,N-dialkyl derivatives thereof.

This invention also relates to the novel processes and the novel intermediates utilized in the production of new aralkylamines, to pharmaceutical formulations of the new aralkylamines and to methods of treating or preventing cardiac arrhythmias using the novel compounds and/or pharmaceutical formulations thereof, described hereinafter.

The new compounds of my invention are 1,2-diaryl derivatives of ethane wherein one of the aryl substituents is an aromatic ring having at least one of its hydrogens replaced by a branched chain aminoalkyl radical and in which the other substituent is a homocyclic or heterocyclic ring selected from aryl, substituted aryl, heterocyclic and substituted heterocyclic substituents.

A preferred group of such compounds includes derivatives in which one or more of the hydrogens of either or both of the phenyl rings is replaced by susbtituents selected from the group consisting of an alkyl group having up to 6 carbon atoms, an alkenyl group having up to 6 carbon atoms, a perfluoroalkyl group having up to 4 carbons atoms, a phenyl or a substituted phenyl radical, an acyl group having up to 4 carbon atoms, a perfluoroacyl group having up to 4 carbon atoms, amino, an alkylamino group having up to 4 carbon atoms, a dialkylamino group having up to 8 carbon atoms, an acylamino group having up to 4 carbon atoms, a perfluoroacylamino group having up to 4 carbon atoms, an alkylsulfonylamino group having up to 4 carbon atoms, halogen (fluorine, chlorine, bromine, or iodine), hydroxyl, an alkoxyl group having up to 4 carbon atoms, a perfluoroalkoxyl group having up to 4 carbon atoms, cyano, carboxy, carbamoyl, an alkylcarbamoyl group having up to 5 carbon atoms, a dialkylcarbamoyl group having up to 9 carbon atoms, a carbalkoxy group having up to 6 carbon atoms, mercapto, an alkylmercapto group having up to 4 carbon atoms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, or a dialkylsulfamoyl group having up to 8 carbon atoms. More than one of these substituents may be on each ring.

An especially preferred group of compounds included within the scope of my invention is represented by the formula

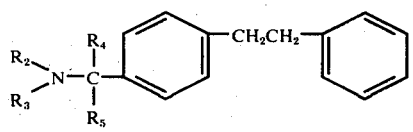

in which $R_4$ and $R_5$ are loweralkyl substituents of from 1–3 carbon atoms; $R_2$ and $R_3$ are either hydrogen, alkyl (preferably of from 1–6 carbon atoms), alkenyl, alkynyl (each preferably of from 1–6 carbon atoms), and can be joined together through an atom of carbon, nitrogen, oxygen or sulfur to form a heterocyclic ring of from 5–6 atoms (such as 1-piperidyl, 1-pyrrolidinyl, 4-morpholinyl, 4-thiomorpholinyl or 1-loweralkyl-4-piperazinyl).

Illustrative of the compounds included within the scope of the invention are α,α-dimethyl-4-phenethylbenzylamine, α,αdiethyl-4-phenethylbenzylamine, α,α-di-n-propyl-4-phenethylbenzylamine, α,α-dimethyl-4-phenethylphenethylamine, α,α-diethyl-4-phenethylphenethylamine, the corresponding N-loweralkyl and the N,N-diloweralkyl derivatives thereof in which the alkyl substituents are either the same or different. Typical of such derivatives are th N-methyl, N-ethyl, N-propyl, N-butyl, N,N-dimethyl, N,N-diethyl, N,N-dipropyl, the N-methyl-N-ethyl, N-ethyl-N-propyl and the N-methyl-N-propyl derivatives thereof.

The compounds represented above, in either their free base or salt form, possess useful pharmacological properties. In particular, they have been found to possess antiarrhythmic acitivity. It has been found that the administration of compounds of the present invention, depicted in the above formula, results in the prevention of arrhythmia in animals under conditions which ordinarily cause the development of arrhythmia in the animal 100% of the time.

It has further been found that administration of the compounds of the present invention will arrest an existing arrhythmia in the animal being treated and cause a resumption of normal cardiac rhythm. as antiarrhythmic agents, these compounds may be administered orally of parenterally. The formulations for administration may be prepared in conventional manner, employing conventional pharmaceutical carriers and excipients.

The non-toxic acid addition salts useful as components in the compositions provided by the present invention are salts formed by the reaction of an equivalent amount of the amine compound of the above formula and an acid which is pharmacologically acceptable in the intended doses. Salts of the above compound which are useful are salts of the amine with hydrochloric acid, hydrobromic acid, sulfuric acid, phosphoric acid, fumaric acid, acetic acid, propionic acid, latic acid, gluconic acid, maleic acid, succinic acid, tartaric acid, and the like. Salts of these acids with the amine base are useful as the active component of the compositions in the method of this invention.

The daily doses are based on the total body weight of the test animal and vary between about 1.00 and 100.00 mg./kg. for mature animals. Thus, a unit does based on four-times-a-day administration is between 2.5 mg. and 250 mg. for a 10 kg. dog, and a total daily dose for a 10 kg. dog would vary between about 10 mg. and 1000 mg. For larger animals, up to 100 kg. and above, proportional dosages ae employed, based on the weight of the animal. Suitable dosage units provided for the administration of the compositions used in the method of the invention are tablets, capsules, (which may be suitably formulated for either immediate or sustained release), syrups, elixirs, parenteral solutions, and the like. These dosage forms preferably contain per unit one or more multiples of the desired dosage unit in combination with the pharmaceutically acceptable diluent or carrier required for preparing the dosage unit.

The compounds represented by the above structural formulae may be prepared as illustrative below:

rolidinyl, morpholinyl, thiomorpholinyl or loweralkyl piperazinyl;

X and X' are selected from the group consisting of hydrogen, halogen (chlorine of fluorine), alkyl (preferably of from 1–6 carbon atoms), alkoxy (preferably of from 1–5 carbon atoms), perfluoroalkyl (e.g. trifluoromethyl), alkylmercapto (preferably of from 1–6 carbon atoms), and dialkylsulfamoyl (preferably of from 2–8 carbon atoms); is an integer selected from the group consisting of 1 to 4 inclusive; and is alkyl (preferably lower alkyl of from 1–6 carbon atoms).

FLOW SHEET 1

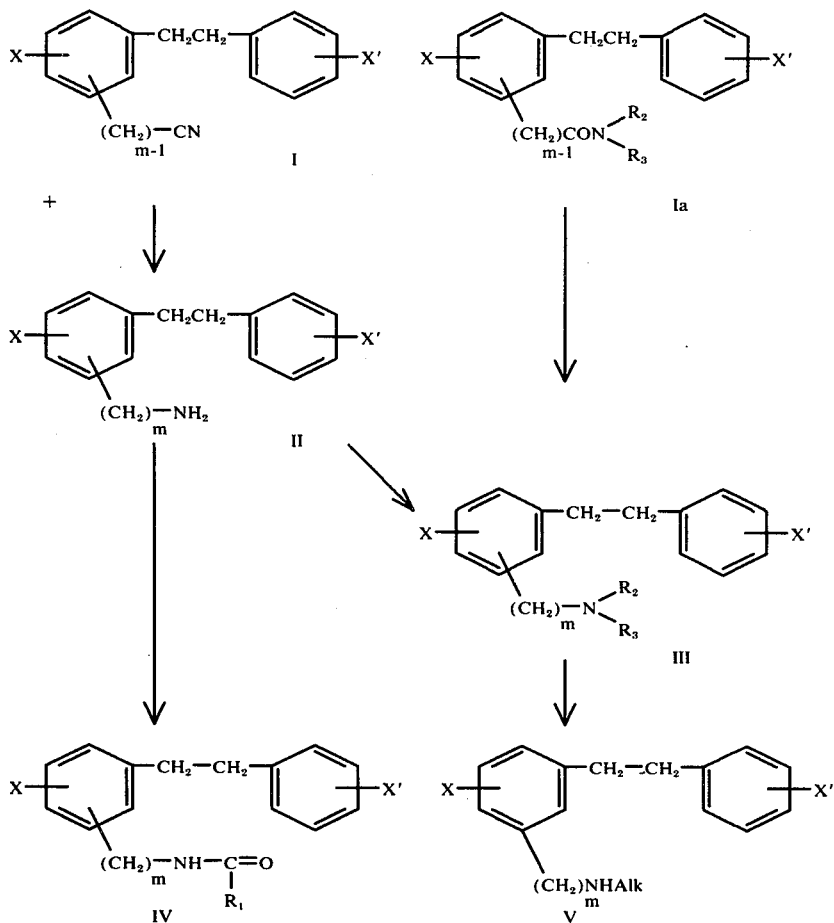

+This step may include a homologation procedure involving conversion of the cyano substituent through the conventional sequence of hydrolysis to the corresponding carboxyl derivative, lithium aluminum hydride reduction to .CH$_2$OH, halogenation to CH$_2$Br and treatment with cyanide ion to the next higher homolog. wherein $R_1$ is hydrogen or lower alkyl (preferably of from 1–5 carbon atoms);

$R_2$ and $R_3$ can be similar or dissimilar and are either hydrogen, alkyl (preferably of from 1–6carbon atoms), aralkyl (preferably benzyl or phenethyl), alkenyl, alkynyl, and can be joined together or with one of methylene carbons bridging the amine substituent and the phenyl ring through an atom of nitrogen, oxygen or sulfur to form a heterocyclic ring of from 5–6 atoms (such as imidazolinyl, piperidyl, pyr- In accordance with the process of our invention, a substituted of unsubstituted benzonitrile or the correspondingly substituted amide Ia having a phenethyl substituent is reduced with an alkali metal hydride to form the corresponding benzylamine. The reduction is preferably effected by contacting the nitrile compound I or the amide Ia in the present of a suitable inert organic solvent, such as tetrahydrofuran, either of other solvents conventionally employed with lithium aluminum hydride. Preferably, this reduction is carried out in the presence of aluminum chloride and an ether compatible with aluminum chloride as a solvent. The temperature at which the reduction is carried out is not critical but it is preferred to employ ambient temperatures and a range of from 0°–50°C. is satisfactory. The resulting benzylamine compound is readily recovered employing conventional techniques.

The corresponding N-(phenethylbenzyl)formamide (IV) is prepared by formylation of the benzylamine compound (II) employing conventional conditions and reagents such as formic acid or esters thereof for this purpose. The resulting formamide derivative can be recovered in conventional manner. The N,N-dimethylamine (III), wherein $R_2$ and $R_3$ each represent methyl, is readily prepared by the treatment of the primary amine compound (II) with formaldehyde and formic acid in accordance with the known Eschweiler-Clarke modification of the Leuckart Reaction. Recovery of the N,N-dimethylamine is accomplished in conventional manner. The N-methyl benzylamine may be prepared by either reduction of the corresponding N-(phenethenyl or phenethynyl-benzyl) formamide (IV) or by monodealkylation of the corresponding N,N-dimethylamine (III) wherein $R_2$ and $R_3$ each represent methyl. Reduction of the formamidomethyl derivative is effected utilizing lithium aluminum hydride under the conditions set forth above for carrying out the reduction of the corresponding benzonitrile (I). Similarly, dealkylation of the N,N-dimethylamine (III) can be effected in known manner such as by treatment with cyanogen bromide followed by hydrolysis of the intermediate cyanamide or by treatment with a haloformate followed by hydrolysis of the resulting urethane intermediate. In each instance, the desired compound can be recovered employing conventional techniques.

The N-loweralkylamines and the N,N-diloweralkylamines corresponding to compounds (V) and (III), respectively, are likewise prepared from the corresponding primary amine (II) by analogous reactions. Thus, the primary amine (II) is treated with a lower aliphatic acid halide or anhydride of from 2–5 carbon atoms, e.g., acetyl chloride, acetic anhydride, propionyl chloride, butyryl chloride or valeryl chloride to produce the N-alkanoyl amide corresponding to (IV) as, for example, the N-acetyl, N-propionyl, N-butyryl of N-valeryl amide. The thus-obtained amide is reduced to the corresponding N-loweralkyl benzylamine compound (V) by reduction with lithium aluminum hydride. The secondary amine compounds (V) produced in this manner are the N-loweralkyl derivatives of 2-phenethylbenzylamines as for example, the N-ethyl, N-propyl, N-butyl and the N-amyl derivatives. The corresponding tertiary amines (III), the N,N-diloweralkyl derivatives, are prepared from the secondary amines by repeating the process employed in the preparation of the secondary amines. Thus, the amides of the secondary amines are prepared and reduced with lithium aluminum hydride to produce the corresponding tertiary amines as, for example, the corresponding N,N-diethyl, N-ethyl-N-methyl, N,N-dipropyl, N,N-dibutyl and the N,N-diamyl derivatives of substituted phenethyl benzylamine.

The corresponding α,α-disubstituted, i.e., dialkyl, compounds are prepared by processes starting from a bromo or iodo substituted diarylalkyl compound. The compounds prepared in accordance with the following processes are, for example, the α,α-dimethyl, α,α-diethyl, α,α-dipropyl, α-methyl-α-ethyl, α-methyl-α-propyl, α-ethyl-α-propyl, α-methyl-α-butyl, and α-methyl-α-isopropyl phenethyl benzylamine. The corresponding N-alkyl or N,N-dialkyl derivatives thereof, e.g., the N-methyl-N-ethyl, N-propyl, N-butyl, N,N-methyl-N-propyl, N-methyl-N-butyl and N-ethyl-N-propyl derivatives are prepared by methods described in the preceding pages for converting the benzylamine into the corresponding N-alkyl or N,N-dialkyl derivatives.

In the process outlined below for producing the α,α-dialkyl substituted benzylamine compounds,

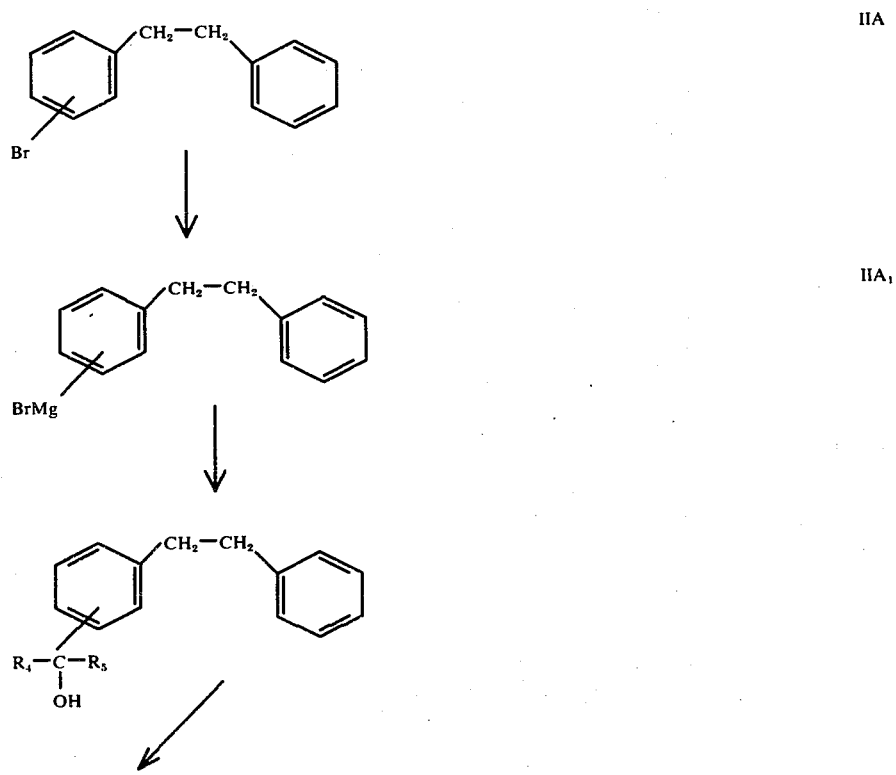

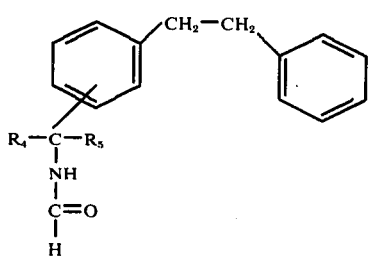 → 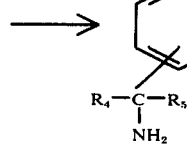 

IIA₃ a 3- or 4- bromo substituted diarylalkyl compound is treated with magnesium under anhydrous conditions to form the Grignard reagent IIA₁ which in turn is treated with an aliphatic ketone such as acetone, diethyl ketone, di-N-propyl ketone or a mixed ketone as, for example, methylethyl ketone, methyl-propyl ketone, methyl-butyl ketone, ethyl-propyl ketone and methyl-isopropyl ketone to produce after hydrolysis the corresponding benzyl alcohol IIA₂ containing alkyl substituents attached to the carbinol carbon of the benzyl alcohol. Alternatively, the 3'- or 4'- alkylphenyl substituted acetophenone is treated with a loweralkyl Grignard reagent to produce after hydrolysis the α,α-dialkyl benzyl alcohol. Alternately, Grignard reagent II₁ is carbonated to produce after hydrolysis the corresponding benzoic acid. This acid is esterified and treated with a lower alkyl Grignard reagent to produce after hydrolysis the α,α-dialkylbenzyl alcohol.

This tertiary alcohol is then employed in a Ritter reaction which involves a rearrangement of a tertiary carbinol or an unsaturated olefin starting material. This starting material is mixed with hydrogen cyanide in aqueous sulfuric acid preferably generated by a mixture of sodium cyanide in a solution of 50–90% aqueous sulfuric acid or other strong inorganic or organic mixtures thereof. The reaction is carried out for a period of 15 minutes to approximately 24 hours, preferably for 9 hours at 0°–50° C. When the compound 2-[4-phenethyl)phenyl]propanol-2 is contacted with a mixture of sodium cyanide and sulfuric acid in acetic acid as the solvent for a period of 1 to 12 hours at 50°C., the product obtained in the intermediate formamide which is readily hydrolyzed to the compound of my invention. The intermediate formamide produced in the foregoing reaction is also accompanied by isolable amounts of a corresponding substituted ethane having an isopropenyl group in place of the α,α-dimethylformamide group. This isopropenyl substituted compound can likewise be submitted to the action of HCN to produce the desired α,α-dimethylformamide intermediate.

In accordance with a still further embodiment of my invention, the compounds having an α,α-diloweralkyl substituted benzylamine may be prepared from the corresponding unsaturated compound by catalytic hydrogenation of the unsaturated linkage according to the following formulae:

wherein R₂, R₃, R₄ and R₅ are as indicated hereinabove.

The acetylenic compounds used as starting materials for this catalytic hydrogenation process are prepared by reaction of the appropriately substituted cuprous phenyl acetylide and an N-formyl-α,α-dialkyl-4-iodo benzylamine to produce an N-formyl-α,α-dialkyl-4-(phenylethynyl)-benzylamine which in turn is either hydrolyzed or reduced with lithium aluminum hydride to produce respectively α,α-dialkyl-4-(phenylethynyl)-benzylamine or the corresponding N-methyl-α,α-dialkyl-4-(phenylethynyl)-benzylamine as illustrated in the following preparations:

PREPARATION 1

α,α-Dimethyl-4-(phenylethynyl)-benzylamine hydrochloride

A. Ethyl-4-iodobenzoate

A solution of 100 grams (0.403 mole) of p-iodobenzoic acid in 600 ml. of absolute ethanol containing 30 ml. of concentrated sulfuric acid is refluxed for 5 days. The cooled solution is poured over 350 grams of ice and is neutralized with saturated sodium carbonate solution. The oil that separates is extracted with six 150 ml. portions of ether. These ether extracts are combined, washed with water, dried over magnesium sulfate, and filtered. Evaporation of the ether gives 131.3 grams, of ethyl-4-iodobenzoate as a chromatographically pure, clear, light oil.

B. α,α-Dimethyl-4-iodobenzyl alcohol

A solution of 2.76 grams of ethyl-4-iodobenzoate in 10 ml. of ether is placed in a dry flask. The solution is cooled in an ice bath and is stirred. Over a 5-minute period, 26.5 ml. of a 1.52 M ethereal solution of methyl magnesium bromide is added. The solution is stirred for 3 hours while in the ice bath. Water (6 ml.) is added dropwise while stirring. The solution is filtered and the filter cake is washed with six 20 ml. portions of ether. The combined ether phases are dried over magnesium sulfate and filtered. Removal of the ether gives α,α-dimethyl-4-iodobenzyl alcohol as a clear, light yellow liquid.

When the above experiment is repeated and ethyl-4-iodobenzoate is allowed to react with ethyl magnesium bromide or N-propyl magensium bromide, the resulting compounds obtained are respectively α,α-diethyl-4-

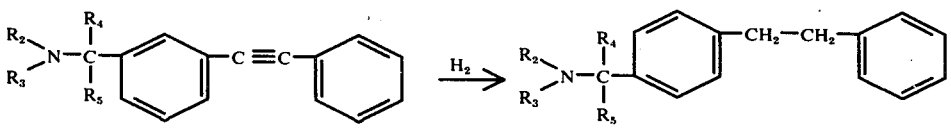

iodobenzyl alcohol or α,α-di(n-propyl)-4-iodobenzyl alcohol.

C. N-Formyl-α,α-dimethyl-4-iodobenzylamine

Into a flask is placed 19 ml. of glacial acetic acid. The flask is cooled in an ice bath and the acetic acid forms a slush. pulverized sodium cyanide (4.18 grams) is added over a 30-minute period while stirring. A precooled solution of 10.3 ml. of concentrated sulfuric acid in 9.5 ml. of glacial acetic acid is added to the stirred cyanide mixture over 15 minutes. The ice bath is removed, and 19.92 grams of α,α-dimethyl-4-iodobenzyl alcohol is added over 10 minutes. The white suspension is stirred 90 minutes and is allowed to stand overnight at room temperature. The reaction mixture is poured over about 100 grams of ice, 100 ml. of water, and 100 ml. of ether. The mixture is neutralized with solid sodium carbonate. The aqueous phase is separated and extracted with two 100 ml. portions of ether. All of the ether phases are combined, washed three times with water, dried over magnesium sulfate, and filtered. Evaporation of the ether gives 18.17 grams of a reddish oil that crystallizes on standing. This solid is triturated with hot hexane and filtered to give N-formyl-α,α-dimethyl-4-iodobenzylamine as a light grey solid. The product may be recrystallized from a benzene-cyclohexane mixture to give white needles, m.p. 121°–125° C.

When the preceding experiment is repeated but utilizing in place of α,α-dimethyl-4-iodobenzyl alcohol either α,α-diethyl-4-iodobenzyl alcohol of α,α-di(n-propyl) -4-iodobenzyl alcohol there is obtained the corresponding N-formyl-α,α-diethyl-4-iodobenzylamine or N-formyl-α,α-di(n-propyl)-4-iodobenzylamine.

D. N-Formyl-α,α-dimethyl-4-(phenylethynyl)-benzylamine

A solution of 1.0 gram of N-formyl-α,α-dimethyl-4-iodobenzylamine in 14 ml. of pyridine is placed in a flask. The solution is stirred under a $N_2$ atmosphere. Cuprous phenylacetylide (0.57 gram) is added to this solution and the mixture is heated in an oil bath at 120°C. At first, the mixture is a yellow suspension, but within 1.5 hours, a homogenous dark amber solution is obtained. The reaction is heated for 10 hours at 120° C. The cooled reaction mixture is poured onto 150 ml. of water and extracted with three 75 ml. portions of a 1:1 ether-benzene mixture. The extracts are combined, washed with two 50 ml. portion of dilute hydrochloric acid, two 50 ml. portions of 5% sodium hydroxide, two 100 ml. portions of water, and dried over magnesium sulfate. After filtration and evaporation of the solvent, there remains 0.78 gram of N-formyl-α,α-dimethyl-4-(phenylethynyl)-benzylamine as a clear oil that crystallizes on standing. The product may be recrystallized from isopropanol, m.p. 135°–141° C.

The experiment is repeated using in place of N-formyl-α, α-dimethyl-4-iodobenzylamine the corresponding N-formyl-α,α-diethyl-4-iodobenzylamine of N-formyl-α,α-di(n-propyl)-4-iodobenzylamine with resultant production of N-formyl-α,α-diethyl-4-(phenylethynyl)-benzylamine of N-formyl-α,α-di(n-propyl)-4-(phenylethynyl)-benzylamine.

E. α,α-Dimethyl-4-(phenylethynyl)-benzylamine hydrochloride

A mixture of 0.50 gram of N-formyl-α,α-dimethyl-4-(phenylethynyl)-benzylamine, 10.7 ml. of glacial acetic acid 6.7 ml. of water, and 1.07 ml. of concentrated hydrochloric acid is stirred and refluxed for 2.5 hours. The solution is evaporated to dryness and α,α-dimethyl-4-(phenylethynyl)-benzylamine hydrochloride is obtained as a light tan solid. The product is recrystalized from an isopropyl alcohol-methanol-ether mixture to give pure α,α-dimethyl-4-(phenylethynyl)-benzylamine hydrochloride, m.p. 275°–278° C. (decomp.).

Analysis calculated for $C_{17}H_{18}NCl$: C, 75.13; H, 6.68; N, 5.15; Cl, 13.04. Found: C, 74.18; H, 6.77; N, 5.30; Cl, 13.11.

When the preceding experiment is repeated using in place of N-formyl-α,α-dimethyl-4-(phenylethynyl)-benzylamine the corresponding N-formyl-α,α-diethyl-4-(phenylethynyl)- benzylamine or N-formyl-α,α-di(n-propyl)-4-(phenylethynyl)- benzylamine there is obtained respectively α,α-diethyl-4-(phenylethynyl)-benzylamine and α,α-di(n-propyl)-4-(phenylethynyl)-benzylamine.

PREPARATION 2

N-α,α-Trimethyl-4-(phenylethynyl)-benzylamine hydrochloride

A solution of 2.92 grams of N-formyl-α,α-dimethyl-4-(phenylethynyl)benzylamine in 30 ml. of benzene is placed in a dry flask. The solution is stirred. A solution of 6.6 grams of 70% ' Red-Al ' solution in benzene is diluted with 30 ml. of benzene; this solution is added dropwise over approximately 30 minutes to the solution of N-formyl-α,α-dimethyl-4-(phenylethynyl)-benzylamine. The reaction is hydrolyzed water and is extracted thoroughly with a 1:1 benzene-ether solvent mixture. The combined extracts are dried over magnesium sulfate, filtered, and the solvent is evaporated to give 3.34 gm. of an oil. This oil is dissolved in ether and treated with ethanolic hydrogen chloride. The precipitate is collected and recrystallized from isopropanol to give N-α,α-trimethyl-4-(phenylethynyl)-benzylamine hydrochloride, m.p. 266°–268° C.

Analysis calculated for $C_{18}H_{19}$ N.HCl: C, 75.64; H, 7.05, N, 4.90. Found: C, 75.72; H, 6.90; N, 4.76.

When the above experiment is repeated using as alternate starting materials either N-formyl-α,α-diethyl-4-phenylethynyl)-benzylamine of N-formyl-α,α-di(n-propyl)-4-(phenylethynyl)-benzylamine there is obtained respectively α,α-diethyl-N-methyl-4-(phenylethynyl)-benzylamine or N-methyl-α,α-di(n-propyl)-4-phenylethynyl benzylamine.

PREPARATION 3

When preparation 1 is repeated utilizing the starting materials indicated the respective indicated products are obtained:

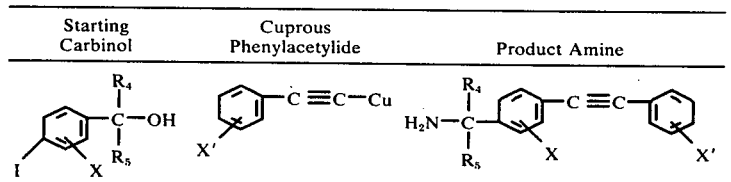

| R₄ & R₅ | X | X' | R₄ & R₅ | X | X' |
| --- | --- | --- | --- | --- | --- |
| methyl | hydrogen | 3-fluoro | methyl | hydrogen | 3-fluoro |
| methyl | hydrogen | 4-fluoro | methyl | hydrogen | 4-fluoro |
| methyl | hydrogen | 2-methoxy | methyl | hydrogen | 2-methoxy |
| methyl | hydrogen | 3-ethoxy | methyl | hydrogen | 3-ethoxy |
| methyl | hydrogen | 4-methoxy | methyl | hydrogen | 4-methoxy |
| methyl | hydrogen | 2-methyl | methyl | hydrogen | 2-methyl |
| methyl | hydrogen | 3-methyl | methyl | hydrogen | 3-methyl |
| methyl | hydrogen | 4-methyl | methyl | hydrogen | 4-methyl |
| methyl | hydrogen | 4-ethyl | methyl | hydrogen | 4-ethyl |
| methyl | hydrogen | 2-hydroxy | methyl | hydrogen | 2-hydroxy |
| methyl | hydrogen | 3-hydroxy | methyl | hydrogen | 3-hydroxy |
| methyl | hydrogen | 4-hydroxy | methyl | hydrogen | 4-hydroxy |
| ethyl | hydrogen | 3-fluoro | ethyl | hydrogen | 3-fluoro |
| ethyl | hydrogen | 4-fluoro | ethyl | hydrogen | 4-fluoro |
| ethyl | hydrogen | 2-methoxy | ethyl | hydrogen | 2-methoxy |
| ethyl | hydrogen | 3-ethoxy | ethyl | hydrogen | 3-ethoxy |
| ethyl | hydrogen | 4-methoxy | ethyl | hydrogen | 4-methoxy |
| ethyl | hydrogen | 2-methyl | ethyl | hydrogen | 2-methyl |
| ethyl | hydrogen | 3-methyl | ethyl | hydrogen | 3-methyl |
| ethyl | hydrogen | 4-methyl | ethyl | hydrogen | 4-methyl |
| ethyl | hydrogen | 4-ethyl | ethyl | hydrogen | 4-ethyl |
| ethyl | hydrogen | 2-hydroxy | ethyl | hydrogen | 2-hydroxy |
| ethyl | hydrogen | 3-hydroxy | ethyl | hydrogen | 3-hydroxy |
| ethyl | hydrogen | 4-hydroxy | ethyl | hydrogen | 4-hydroxy |
| methyl | 3-fluoro | hydrogen | methyl | 3-fluoro | hydrogen |
| methyl | 4-fluoro | hydrogen | methyl | 4-fluoro | hydrogen |
| methyl | 2-methoxy | hydrogen | methyl | 2-methoxy | hydrogen |
| methyl | 3-ethoxy | hydrogen | methyl | 3-methoxy | hydrogen |
| methyl | 4-methoxy | hydrogen | methyl | 2-methyl | hydrogen |
| methyl | 2-methyl | hydrogen | methyl | 3-methyl | hydrogen |
| methyl | 3-methyl | hydrogen | methyl | 4-methyl | hydrogen |
| methyl | 4-methyl | hydrogen | methyl | 4-methyl | hydrogen |
| methyl | 4-ethyl | hydrogen | methyl | 4-ethyl | hydrogen |
| methyl | 2-hydroxy | hydrogen | methyl | 2-hydroxy | hydrogen |
| methyl | 3-hydroxy | hydrogen | methyl | 3-hydroxy | hydrogen |
| methyl | 4-hydroxy | hydrogen | methyl | 4-hydroxy | hydrogen |
| methyl | hydrogen | 4-methyl-sulfonyl | methyl | hydrogen | 4-methyl-sulfonyl |
| methyl | hydrogen | 4-methyl-mercapto | methyl | hydrogen | 4-methyl-mercapto |
| methyl | hydrogen | 4-trifluoromethyl | methyl | hydrogen | 4-trifluoromethyl |

EXAMPLE 1

α,α-DIMETHYL-4-PHENETHYLBENZYLAMINE HYDROCHLORIDE

A mixture of 0.45 gram of α,α-dimethyl-4-(phenylethynyl)-benzylamine hydrochloride, 61 ml. of absolute methanol, and 163 mg. of platinum dioxide catalyst is hydrogenated at 40 p.s.i. for one hour. The hydrogenation is stopped, the catalyst is removed by filtration, and the methanol is removed by evaporation. The residue is partitioned between benzene and 10% sodium hydroxide solution. The benzene phase is washed well with water, dried over magnesium sulfate, filtered, and the benzene is evaporated. The residual oil is dissolved in ether and treated with ethanolic hydrogen chloride. The precipitate is collected and recrystallized from isopropanol and ether to give α,α-dimethyl-4-phenethylbenzylamine hydrochloride, m.p. 225°–228° C.

Analysis calculated for $C_{17}H_{22}ClN$: C, 74.03; H, 8.04; N, 5.08. Found: C, 73,81; H, 8.06; N, 4.96.

When the preceding experiment is repeated using the products produced in accordance with Preparations 1, 2 and 3 hereinabove, the correspondingly substituted α,α-dialkyl phenethylbenzylamine is obtained.

What is claimed is:

1. A compound of the formula

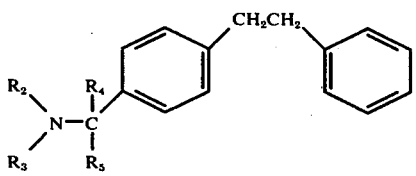

wherein
R₂ and R₃ are each members of the group consisting of hydrogen and loweralkyl and
R₄ and R₅ are loweralkyl substituents of from 1–3 carbon atoms;
or a derivative of said compound in which one of the hydrogens of the benzene ring is replaced by halogen, loweralkyl, loweralkoxy, perfluoroloweralkyl, loweralkylmercapto or loweralkysulfonyl.

2. A compound of the formula

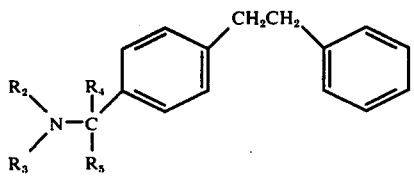

wherein

R$_2$ and R$_3$ are each members of the group consisting of hydrogen and loweralkyl and R$_4$ and R$_5$ are loweralkyl substituents of from 1-3 carbon atoms.

3. α,α-Dimethyl-4-phenethylbenzylamine.

4. The N-methyl derivative of α,α-dimethyl-4-phenethylbenzylamine.

5. The N,N-dimethyl derivative of α,α-dimethyl-4-phenethylbenzylamine.

6. The non-toxic acid addition salts of the compounds of claim 1.

7. The non-toxic acid addition salts of the compounds of claim 2.

8. The non-toxic acid addition salts of α,α-dimethyl-4-phenethylbenzylamine, N-methyl-α,α-dimethyl-4-phenethylbenzylamine or N,N-dimethyl-α,α,-dimethyl-phenethylbenzylamine.

9. The salts of claim 8 wherein said acid is HCl.

* * * * *